(12) United States Patent
Lacher et al.

(10) Patent No.: US 10,130,257 B2
(45) Date of Patent: Nov. 20, 2018

(54) ACCESS SYSTEM FOR A MOTOR VEHICLE

(71) Applicant: Audi AG, Ingolstadt (DE)

(72) Inventors: Peter Lacher, Gaimersheim (DE);
Sebastian Steinhorst, Glandorf (DE)

(73) Assignee: AUDI AG, Ingolstadt (DE)

( * ) Notice: Subject to any disclaimer, the term of this patent is extended or adjusted under 35 U.S.C. 154(b) by 0 days.

(21) Appl. No.: 15/763,084

(22) PCT Filed: Nov. 7, 2016

(86) PCT No.: PCT/EP2016/076784
§ 371 (c)(1),
(2) Date: Mar. 23, 2018

(87) PCT Pub. No.: WO2017/092971
PCT Pub. Date: Jun. 8, 2017

(65) Prior Publication Data
US 2018/0256027 A1    Sep. 13, 2018

(30) Foreign Application Priority Data

Dec. 4, 2015 (DE) .......... 10 2015 015 741

(51) Int. Cl.
*A61B 5/00* (2006.01)
*A61B 5/024* (2006.01)
(Continued)

(52) U.S. Cl.
CPC ............ *A61B 5/0008* (2013.01); *A61B 5/024* (2013.01); *A61B 5/1171* (2016.02); *A61B 5/681* (2013.01);
(Continued)

(58) Field of Classification Search
CPC combination set(s) only.
See application file for complete search history.

(56) References Cited

U.S. PATENT DOCUMENTS 7,138,904 B1   11/2006  Dutu
8,461,998 B2    6/2013  Ruhs et al.
(Continued)

FOREIGN PATENT DOCUMENTS

CN    101114401 A    1/2008
DE     10349165 A1   5/2005
(Continued)

OTHER PUBLICATIONS

International Search Report and Written Opinion of the International Searching Authority directed to related International Application No. PCT/EP2016/076784, dated Jan. 31, 2017, with attached English-language translation; 26 pages.

(Continued)

*Primary Examiner* — Travis R Hunnings
(74) *Attorney, Agent, or Firm* — Sterne, Kessler, Goldstein & Fox P.L.L.C.

(57) ABSTRACT

A wrist computer to be worn on an arm of a user, comprising a detection device configured to detect at least one vital parameter of the user, and a radio module configured to, when activated, establish and maintain a wireless data connection to a radio module of another object, wherein the wrist computer comprises a control unit configured to activate the radio module of the wrist computer when the at least one vital parameter of the user is detected by the detection device, and to deactivate the radio module of the wrist computer when the at least one vital parameter of the user is no longer detected by the detection device.

6 Claims, 1 Drawing Sheet

(51) Int. Cl.
  *A61B 5/1171*    (2016.01)
  *B60R 25/25*     (2013.01)
(52) U.S. Cl.
  CPC ............ *A61B 5/6843* (2013.01); *B60R 25/25* (2013.01); *A61B 2560/0209* (2013.01)

(56) References Cited

U.S. PATENT DOCUMENTS

| | | |
|---|---|---|
| 9,275,208 B2 | 3/2016 | Protopapas |
| 2010/0148923 A1 | 6/2010 | Takizawa |
| 2013/0217979 A1 | 8/2013 | Blackadar et al. |
| 2014/0081155 A1 | 3/2014 | Coggins |
| 2015/0081169 A1 | 3/2015 | Pisz |
| 2015/0087919 A1 | 3/2015 | Johnson et al. |
| 2015/0314681 A1 | 11/2015 | Riley, Sr. et al. |
| 2016/0199002 A1* | 7/2016 | Lee ...................... A61B 5/0008 340/870.07 |
| 2016/0371907 A1* | 12/2016 | Ma .......................... E05B 81/82 |
| 2018/0056784 A1* | 3/2018 | Virgilio ................. B60K 28/02 |

FOREIGN PATENT DOCUMENTS

| | | |
|---|---|---|
| DE | 202006011486 U1 | 10/2006 |
| DE | 102009002906 A1 | 11/2010 |
| DE | 102014204882 A1 | 9/2014 |

OTHER PUBLICATIONS

International Preliminary Report on Patentability directed to related International Patent Application No. PCT/EP2016/076784, dated Oct. 26, 2017, with attached English-language translation; 22 pages.

* cited by examiner

ACCESS SYSTEM FOR A MOTOR VEHICLE

TECHNICAL FIELD

This disclosure relates to an access system for a motor vehicle, comprising a wrist computer to be worn on an arm of a user.

BACKGROUND

Wrist computers to be worn on an arm of a user, for example in the form of what are known as smart watches, are known per se. Such smart watches usually involve a wristwatch, which furthermore comprises sensors, actuators, and additional computer functionalities and connectivity functions. In addition to the time, smart watches can frequently display further information and can be individually equipped by the user with new functions via additional programs, known as apps.

CN 101114401 A, for example, shows a wrist computer to be worn on an arm of a user, which is designed to detect a pulse of the user and, in the event of irregularities, to automatically connect via a Bluetooth connection to a mobile telephone, for example, to send an emergency call.

DE 20 2006 011 486 U1 shows a GPS receiver, which can transmit GPS data via a Bluetooth interface. The GPS receiver includes an automatic power save function. An installed electronics system switches the GPS receiver off when a vehicle in which the GPS receiver is installed is stationary. As soon as the vehicle moves, the power supply of the GPS receiver is switched back on.

DE 103 49 165 A1 shows headphones able to wirelessly, for example, via a Bluetooth connection, receive pulse data detected by way of a chest strap equipped with a pulse sensor.

US 2015/0087919 A1 describes a smart watch comprising different sensors for measuring vital parameters. The smart watch can additionally comprise a sensor by way of which it can be ascertained whether the shape of the wristband of the smart watch has been altered. Based thereon, it is possible to determine whether a user has put on the smart watch. As soon as it has been determined in this way that the smart watch has been put on, the smart watch is automatically activated.

US 2010/0148923 A1 describes a biometric authentication system of a motor vehicle. The authentication system is used to lock and unlock the motor vehicle, and to start an engine of the motor vehicle. For this purpose, the authentication system uses biometric data of a user to check whether this is an authorized user. An on-board camera, for example, can be used to detect a face of the user or an iris of the user. Additionally, a sensor system disposed in a door handle or a start switch can be used to acquire fingerprints or vein information about the user.

BRIEF DESCRIPTION OF THE DRAWINGS/FIGURES

The accompanying drawings are incorporated herein and form a part of the specification.

In the drawings, like reference numbers generally indicate identical or similar elements.

DETAILED DESCRIPTION

Figure 1:
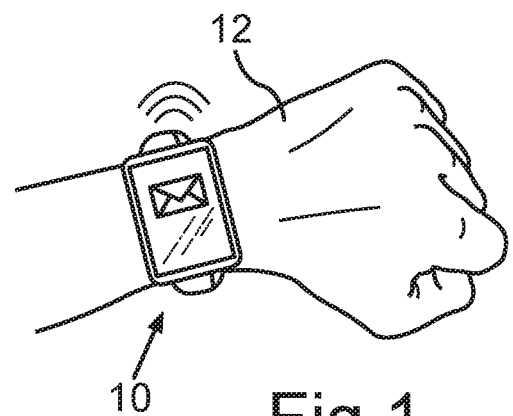
FIG. 1 shows an exemplary wrist computer, configured as a smart watch, to be worn on an arm of user, according to some embodiments.

It is the object of the this disclosure to enable a particularly energy-efficient operation of a wrist computer configured to be worn on an arm of a user.

This object is achieved by an access system for a motor vehicle, comprising a wrist computer to be worn on an arm of a user having the features of the independent claim(s). Advantageous embodiments along with useful and essential refinements are disclosed in the dependent claims.

The access system for a motor vehicle, according to this disclosure, comprises a wrist computer to be worn on an arm of a user, the wrist computer comprising a detection device configured to detect at least one vital parameter of the user. Furthermore, the wrist computer comprises a radio module, which, when activated, is configured to establish and maintain a wireless data connection to a radio module of another object. The wrist computer of the access system further comprises a control unit, which is configured to activate the radio module of the wrist computer as soon as the at least one vital parameter of the user is detected by the detection device, and to deactivate the radio module of the wrist computer as soon as the at least one vital parameter of the user is no longer detected by the detection device.

This disclosure is based on the finding that permanently active wireless data connections usually consume a relatively large amount of energy. In the case of wrist computers to be worn on the arm, such as in the form of smart watches, the need to establish and maintain a wireless data connection between the wrist computer and another object, and in particular an electronic device, often only exists when the wrist computer is in fact worn on the wrist.

It is therefore provided according to the disclosure herein that the radio module is only activated, and maintained in this activated state, while the at least one vital parameter of the user is being detected by the detection device. The detection device is configured to detect the at least one vital parameter of the user at least while at least a part of the wrist computer connected to the detection device is in contact with the arm of the user. As soon as the wrist computer is no longer worn on the arm of the user, the radio module of the wrist computer is deactivated. As soon as the wrist computer is put on the arm of the user again and worn, this is detected by the detection device, as configured to detect at least one vital parameter of the user. The radio module is thus activated again as soon as the wrist computer has again been put on the arm of the user. Since the radio module of the wrist computer is only switched to the active state when the wrist computer is in fact being worn on the arm of a user, and is thus being used, a large amount of energy can be saved. The duration of use of the wrist computer can thereby be considerably extended.

One advantageous embodiment of the wrist computer provides for the detection device to comprise a pulse sensor, which is configured to detect a pulse of the user. Wrist computers configured as smart watches are usually worn on the wrist. By way of the pulse sensor, it can thus be established in a particularly simple manner whether the wrist computer has just been put or taken off by the user. As a result, the activation and deactivation of the radio module of the wrist computer can always take place in a precisely tailored manner, namely when the wrist computer has been put on or taken off the arm of the user.

A further advantageous embodiment of the wrist computer provides for the detection device to comprise a temperature sensor, which is configured to detect a skin temperature of the user. For example, a target skin temperature of 21 to 35° C., for example, may be stored in a memory of the wrist computer. As long as the temperature sensor ascertains that the ascertained temperature agrees at least substantially with this target temperature, it is assumed that the wrist computer is being worn on the arm of the user. It is likewise possible in a simple manner, by way of the temperature sensor ascertaining the skin temperature of the user, to determine whether or not the wrist computer is being worn on the arm. The activation and deactivation of the radio module of the wrist sensor can therefore likewise take place in a precisely tailored manner.

According to a further advantageous embodiment of the wrist computer, it is provided that the radio module is configured to establish and maintain the wireless connection in the form of a Bluetooth connection. Compared to other wireless connections, establishing and maintaining a Bluetooth connection requires relatively little energy, has relatively low susceptibility to faults, and requires a relatively low transmission power.

According to a further advantageous embodiment of the wrist computer, it is provided that the radio module of the wrist computer is configured to transmit a user identification via the wireless data connection to a radio module of a motor vehicle. The wrist computer can thus be used particularly easily for authentication purposes, for example, in connection with the use of the motor vehicle.

The access system according to this disclosure for a motor vehicle comprises the wrist computer disclosed herein, or an advantageous embodiment of the disclosed wrist computer, a locking system on board the vehicle for locking and unlocking the motor vehicle, a radio module on board the vehicle, and a biometric access device on board the vehicle. The biometric access device is configured to actuate the locking device for locking and/or unlocking the motor vehicle only when a predefined biometric feature of a person has been detected by the biometric access device, and when a user identification associated with the person has been transmitted by way of the radio module of the wrist computer via a wireless connection to the radio module on board the vehicle. As a result of the integration of the wrist computer disclosed herein in the access system for the motor vehicle, a particularly secure access system can be provided. The biometric access device preferably comprises a hand vein scanner. When a biometric access system, such as a hand vein scanner, is used, the motor vehicle usually must have knowledge of the identity of the person before this person is able to authenticate himself or herself to the motor vehicle, so as to allow a verification to be carried out. Furthermore, such an access system is usually also only activated when a person authorized to authenticate himself or herself approaches the vehicle, and not just any passer-by. The identification using the wrist computer according to the invention preferably takes place via Bluetooth. However, it is a disadvantage of such an identification that it is not possible to precisely determine the position of the person. As a result, it is not possible to distinguish whether the person is presently located in the motor vehicle or outside the motor vehicle. If the motor vehicle is to be locked via the hand vein scanner, it is particularly advantageous if it can be ensured that the wrist computer is not located inside the motor vehicle. Because the wireless connection, preferably in the form of the Bluetooth connection, is deactivated as soon as the wrist computer is taken off, the motor vehicle can no longer be locked when a vehicle occupant has taken off the wrist computer prior to exiting the motor vehicle. In this way, locking the vehicle occupant out inadvertently can be effectively prevented.

In a method for operating a wrist computer to be worn on an arm of a user, at least one vital parameter of the user is detected by way of a detection device, and a wireless connection to a radio module of another object is established and maintained by a radio module of the wrist computer as long as the radio module of the wrist computer is activated. The method provides that the radio module of the wrist computer is activated by a control unit of the wrist computer as soon as the at least one vital parameter of the user is detected by the detection device, and the radio module of the wrist computer is deactivated by the control unit as soon as the at least one vital parameter of the user is no longer detected by the detection device.

Further advantages, features and details of this disclosure will be apparent from the following description of a preferred exemplary embodiment and based on the drawings. The features and feature combinations mentioned above in the description, and the features and feature combinations mentioned hereafter in the description of the figures and/or shown only in the figures, can be used not only in the respective indicated combination, but also in other combinations, or alone, without departing from the scope of the invention.

Figure 2:
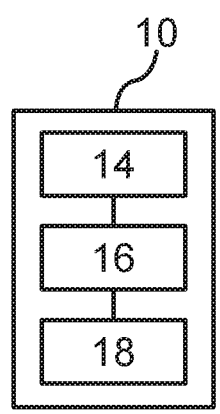
FIG. 2 shows a schematic illustration of the smart watch, which comprises a radio module, a control unit, and a detection device for pulse detection, according to some embodiments.
Figure 3:
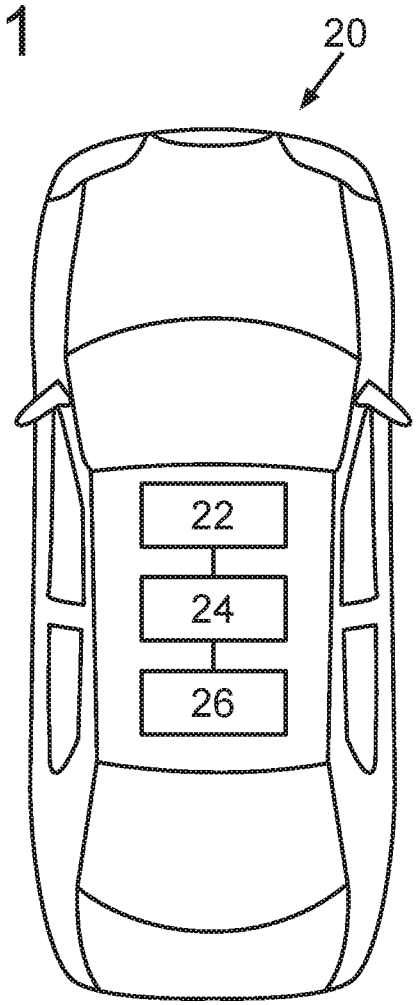
FIG. 3 shows a schematic illustration of an exemplary motor vehicle, which comprises a locking device for locking and/or unlocking the motor vehicle, a radio module, and a biometric access device, according to some embodiments.

In the drawings:

FIG. 1 shows a wrist computer, configured as a smart watch, to be worn on an arm of user, according to some embodiments;

FIG. 2 shows a schematic illustration of the smart watch, which comprises a radio module, a control unit, and a detection device for pulse detection, according to some embodiments; and FIG. 3 shows a schematic illustration of a motor vehicle, which comprises a locking device for locking and/or unlocking the motor vehicle, a radio module, and a biometric access device, according to some embodiments.

A wrist computer, configured as a smart watch 10, to be worn on an arm 12 of a user is shown in a perspective view in FIG. 1. The smart watch is a wristwatch, which furthermore comprises sensors, actuators, such as a vibration motor and the like, and additional computer functionalities and connectivity functions. In addition to displaying the time, the smart watch 10 can represent a plurality of other pieces of information and can be individually equipped by the user with new functions via additionally installable programs, known as apps.

FIG. 2 shows a schematic illustration of the smart watch 10. The smart watch 10 comprises a radio module 14, a control unit 16, and a detection device 18. The detection device 18 is configured to detect a pulse of the user as soon as the smart watch 10 has been put on the arm 12 of the user. For this purpose, the detection device 18 comprises at least one pulse sensor.

When activated, the radio module 14 is configured to establish and maintain a wireless connection to a radio module of another object. The radio module 14 is a Bluetooth module, which is configured to establish and maintain said wireless connection in the form of a Bluetooth connection. The control unit is configured to activate the radio module 14 of the smart watch 10 as soon as a pulse of the user wearing the smart watch 10 on the arm 12 is detected by the detection device 18. The control unit 16 is furthermore configured to deactivate the radio module 14 of the smart watch 10 as soon as a pulse is no longer detected by the detection device 18. Thus, when the user takes the smart watch 10 off the arm 12, the detection device 18 can no longer detect a pulse. The control unit 16 thereupon deactivates the radio module 14, whereby the radio module 14 serving as a Bluetooth adapter is deactivated and all previously active connections are cut. As soon as the user puts the smart watch 10 back on the arm 12, the detection device 18 detects the pulse of the user, whereupon the radio module 14 is activated again.

FIG. 3 shows a schematic top view of a motor vehicle 20. The motor vehicle 20 comprises an on-board locking device 22 for locking and unlocking the motor vehicle 20. Furthermore, the motor vehicle 20 comprises an on-board biometric access device 24 and an on-board radio module 26. The smart watch 10 can establish a Bluetooth connection to the radio module 26 of the motor vehicle 10 via the radio module 14 and then transmit a user identification to the on-board radio module 26. The smart watch 10, the on-board locking device 22, the on-board biometric access device 24, and the on-board radio module 26 together form an access system for the motor vehicle 20.

The biometric access device 24 is a hand vein scanner, by way of which a user can authenticate himself or herself for locking and unlocking the motor vehicle 20.

The biometric access device 24 is configured to actuate the locking device 22 for locking and/or unlocking the motor vehicle 20 only when a predefined biometric feature of a person has been detected by the biometric access device 24, and a user identification associated with the person has been transmitted to the on-board radio module 26 by way of the radio module 14 of the smart watch 10 via a wireless connection, and preferably via Bluetooth.

When a person desires to lock the motor vehicle 20 from the outside, the person must undergo hand vein scanning for authentication purposes, and additionally a corresponding user identification must have been received by the on-board radio module 26 from the smart watch 10.

If the person takes off the smart watch 10 while driving the motor vehicle 20, the radio module 14 of the smart watch 10 is deactivated. When the vehicle occupant now exits the motor vehicle 20 and would like to lock the motor vehicle by way of hand vein identification, the motor vehicle will not be locked because the radio module 14 of the smart watch 10 is deactivated, and thus the user identification cannot be transmitted to the on-board radio module 26. As a result, the person cannot inadvertently lock himself or herself out of the motor vehicle 20 if the smart watch 10 was accidentally left in the motor vehicle 20.

The invention claimed is:

1. An access system for a motor vehicle, comprising:
   a wrist computer to be worn on an arm of a user, comprising:
      a detection device, configured to:
         detect at least one vital parameter of the user;
      a radio module, configured to:
         when activated, establish and maintain a wireless data connection to a radio module of another object;
      a control unit, configured to:
         activate the radio module of the wrist computer when the at least one vital parameter of the user is detected by the detection device; and
         deactivate the radio module of the wrist computer when the at least one vital parameter of the user is no longer detected by the detection device;
   a locking device of the motor vehicle for locking and unlocking the motor vehicle;
   a radio module of the motor vehicle; and
   a biometric access device of the motor vehicle, configured to:
      actuate the locking device of the motor vehicle for locking or unlocking the motor vehicle when a predefined biometric feature of a person has been detected by the biometric access device and a user identification associated with the person has been transmitted to the radio module of the motor vehicle by way of the radio module of the wrist computer via the wireless data connection.

2. The access system of claim 1, wherein the biometric access device comprises a hand vein scanner.

3. The access system of claim 1, wherein the detection device comprises a pulse sensor configured to detect a pulse of the user.

4. The access system of claim 1, wherein the detection device comprises a temperature sensor configured to detect a skin temperature of the user.

5. The access system of claim 1, wherein the radio module of the wrist computer is configured to establish and maintain the wireless data connection via a Bluetooth connection.

6. The access system of claim 1, wherein the radio module of the wrist computer is configured to transmit the user identification via the wireless data connection to the radio module of the motor vehicle.

* * * * *